(12) United States Patent
Johdo et al.

(10) Patent No.: US 6,747,012 B1
(45) Date of Patent: Jun. 8, 2004

(54) CRYSTALLINE ANTHRACYCLINE ANTIBIOTIC AND PROCESS FOR PRODUCING THE SAME

(75) Inventors: Osamu Johdo, Fujisawa (JP); Kiyotomo Nakamura, Yatsushiro (JP); Takeo Yoshioka, Ayase (JP)

(73) Assignee: Mercian Corporation, Tokyo (JP)

( * ) Notice: Subject to any disclaimer, the term of this patent is extended or adjusted under 35 U.S.C. 154(b) by 0 days.

(21) Appl. No.: 09/555,494

(22) PCT Filed: Dec. 1, 1998

(86) PCT No.: PCT/JP98/05391

§ 371 (c)(1),
(2), (4) Date: Jun. 1, 2000

(87) PCT Pub. No.: WO99/29708

PCT Pub. Date: Jun. 17, 1999

(30) Foreign Application Priority Data

Dec. 5, 1997 (JP) .............................................. 9-350157

(51) Int. Cl.$^7$ ......................... A01N 43/04; A01N 63/02
(52) U.S. Cl. ......................................... 514/34; 424/780
(58) Field of Search .................. 536/16–18.5; 424/180, 424/780; 514/34

(56) References Cited

U.S. PATENT DOCUMENTS

| 4,012,448 A | * | 3/1977 | Smith et al. ................. 260/591 |
| 4,025,623 A | * | 5/1977 | Arcamone et al. .......... 424/180 |
| 4,201,773 A | * | 5/1980 | Horton et al. ............... 424/180 |
| 4,592,999 A | * | 6/1986 | Umezawa et al. ............. 435/78 |
| 4,861,870 A | | 8/1989 | Oppico et al. ............. 536/16.9 |

FOREIGN PATENT DOCUMENTS

| JP | 59-118797 | 7/1984 |
| JP | 5-399 | 1/1993 |

* cited by examiner

Primary Examiner—Bradley L. Sisson
(74) Attorney, Agent, or Firm—Wenderoth, Lind & Ponack, L.L.P.

(57) ABSTRACT

Disclosed are a crystalline form of anthracycline antibiotic having specific characteristic 2θ values as measured by the X-ray diffraction method, and a process for producing the crystalline form. This process comprises the step of crystallization involving the combined use of a specific poor solvent for the antibiotic and a good solvent thereof. This crystalline form has excellent chemical and physical properties.

6 Claims, 1 Drawing Sheet

CRYSTALLINE ANTHRACYCLINE ANTIBIOTIC AND PROCESS FOR PRODUCING THE SAME

TECHNICAL FIELD

This invention relates to novel crystalline forms of an anthracycline antibiotic, particularly daunomycin (also known as daunorubicin), and a process for producing the same.

BACKGROUND ART

Daunomycin (also known as daunorubicin; hereinafter abbreviated as DM), which is an anthracycline antibiotic represented by the following formula (I)

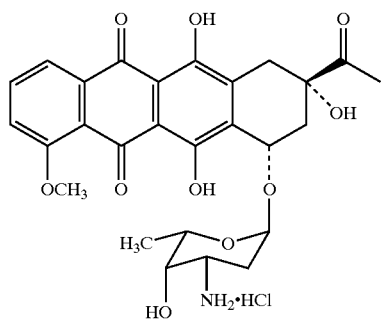

is known to be obtained from a culture medium of an actinomycete, and has a wide anticancer spectrum against experimental animal tumors. As a matter of fact, DM is being widely used as a chemo-therapeutic agent for cancer in clinical applications.

However, the currently available bulk form of DM (DM hydrochloride) is an amorphous powder or a solid which is tentatively classified as crystalline but has high hygroscopicity and poor stability. From the viewpoint of the preparation of DM into medicines, the physical and chemical properties of not only its final bulk powder but also its intermediate products have a great significance. For example, poor chemical stability requires great caution in storage, and high hygroscopicity makes its handling difficult. Moreover, with consideration for its use as a drug, any residual solvent may constitute a fatal shortcoming.

Accordingly, an object of the present invention is to provide a solid product of DM hydrochloride having excellent chemical stability and, preferably, further having low hygroscopicity and an allowable residual solvent content.

DISCLOSURE OF THE INVENTION

The present inventors made repeated investigations with a view to solving the above-described problems and have now found that the crystallization of DM hydrochloride by using a certain solvent system yields a specific crystalline form of DM hydrochloride having excellent chemical stability and, in some instances, this crystalline form also has low hygroscopicity and can solve the problem with residual solvent.

Thus, according to the present invention, there is provided a crystalline form of DM hydrochloride having at least characteristic 2θ values (in degrees) of 6.18, 7.88, 9.82, 11.60, 13.30, 15.80, 20.88 and 23.12 as measured by the X-ray powder diffraction method.

According to the present invention, there is also provided a process for producing the aforesaid crystalline form of DM hydro-chloride from a solution containing DM hydrochloride, the process comprising the steps of preparing the aforesaid solution by using a solvent system composed of a poor solvent for the antibiotic and a good solvent which is miscible with the poor solvent and capable of dissolving the antibiotic; and subjecting the solution so prepared to a crystallization treatment.

SPECIFIC DESCRIPTION OF THE INVENTION

Figure 1:
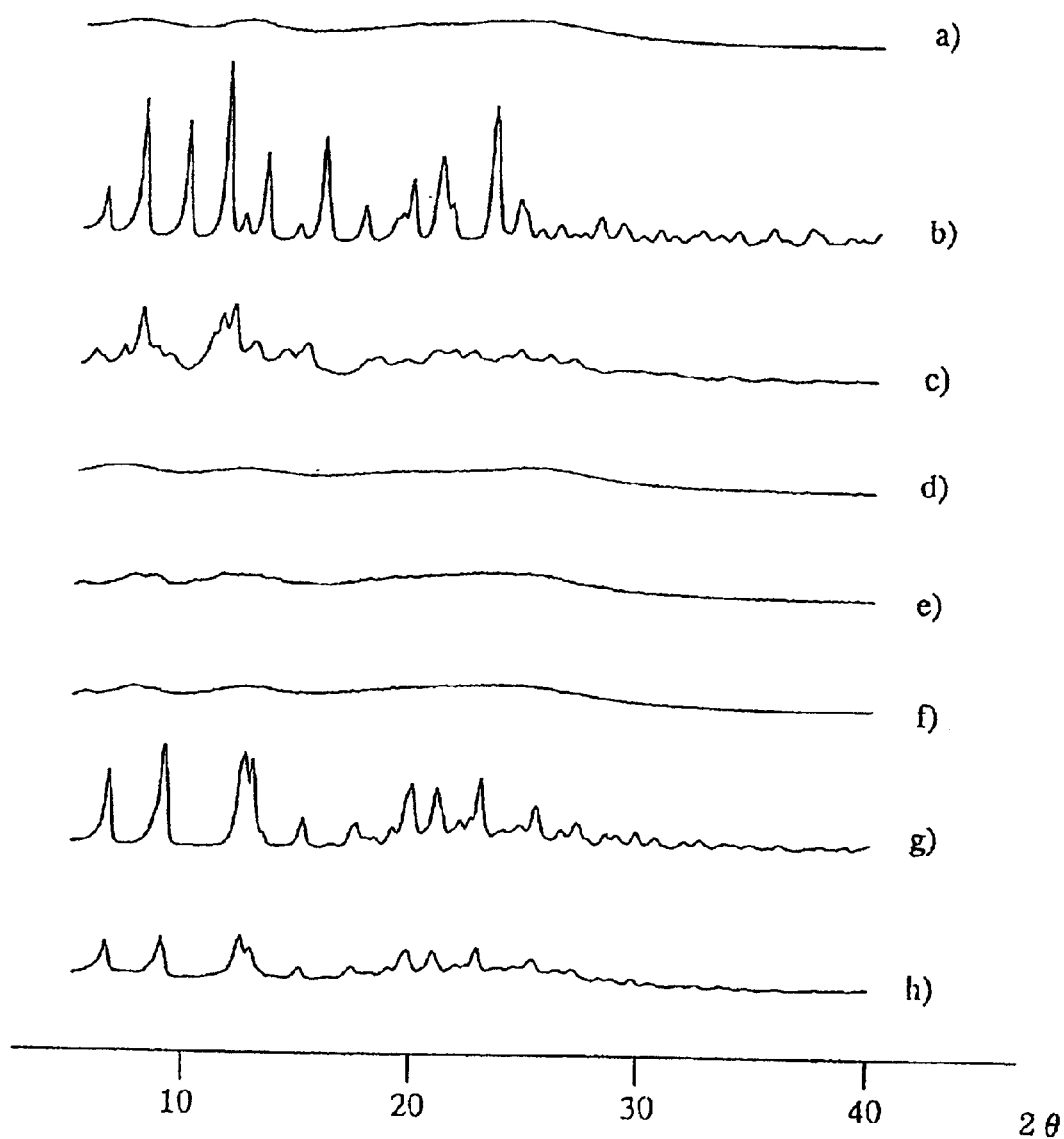
FIG. 1 is a chart showing the results of X-ray powder diffraction analysis of DM hydrochloride powders and various crystalline forms of DM hydrochloride. In this chart, b) shows the result of X-ray powder diffraction analysis of a crystalline form of DM hydrochloride in accordance with the present invention; a), d), e) and f) show the results of X-ray powder diffraction analysis of amorphous DM hydrochloride powders (comparative powders); and c), g) and h) show the results of X-ray powder diffraction analysis of solid forms of DM hydrochloride which are regarded as crystalline but do not show the properties of the crystalline form in accordance with the present invention (comparative crystalline forms).

Specifically, the crystalline form of DM hydrochloride in accordance with the present invention are characterized by having at least characteristic 2θ values (in degrees) of 6.18, 7.88, 9.82, 11.60, 13.30, 15.80, 20.88 and 23.12 as measured by the X-ray powder diffraction method (the Debye-Scherrer method) [see b) in FIG. 1]. The term "crystalline form" as used herein means a single crystal or a mass of such crystals, and the aforesaid results of X-ray powder diffraction analysis are those obtained from such masses.

The crystalline form in accordance with the present invention are clearly distinguished from amorphous powders [corresponding to those shown as a), d), e) and f) in FIG. 1] and solid forms tentatively regarded as crystalline [corresponding to those shown as c), g) and h) in FIG. 1]. Moreover, as will be described later, the crystalline form b) have very excellent properties from the viewpoints of hygroscopicity, residual solvent and chemical stability.

Generally and not by way of limitation, the process for producing the aforesaid crystalline form in accordance with the present invention comprises the steps of preparing a solution by dissolving a DM hydrochloride powder having a relative purity of greater than 90% in a solvent capable of dissolving the DM; and crystallizing the DM by adding to the solution a solvent which is miscible with the aforesaid solvent but is a poor solvent for DM.

It is important to use a solvent containing at least 1-butanol as the aforesaid poor solvent. Typical examples of such solvents include 1-butanol alone and solvent mixtures composed of 1-butanol and other organic solvents (e.g., acetone, hexane and diisopropyl ether). On the other hand, as the solvent capable of dissolving DM, there may be used any solvent that can dissolve DM, is miscible the aforesaid poor solvent, and hence suits the purpose of the present invention. Typical examples of such solvents include, but are not limited to, water, methanol, ethanol and mixtures of two or more of them.

In accordance with a preferred embodiment, the production process of the present invention comprises the steps of preparing a solution by dissolving a DM hydrochloride powder having a relative purity of greater than 90% in methanol (for example, by using the DM hydrochloride powder and methanol in a weight ratio of 1:5 to 1:20); and crystallizing the DM by adding 1-butanol or a mixture of 1-butanol and acetone, hexane or diisopropyl ether (for example, containing up to 60% of acetone, hexane or diisopropyl ether) to the aforesaid solution in an amount of about 1 to 20 parts by volume as based on the methanol.

When the expression "1-butanol/acetone", for example, is used in connection with the present invention, it means the combined use of 1-butanol and acetone. Thus, according to the present invention, the solvent used to dissolve a DM hydrochloride powder may comprise not only methanol alone, but also a mixture of methanol and 1-butanol or a mixture of methanol 1-butanol and acetone, hexane or diisopropyl ether, provided that the mixture can dissolve the DM hydrochloride powder. Then, as a solvent for crystallization purposes, 1-butanol or a mixture of 1-butanol and acetone, hexane or diisopropyl ether is added to the DM hydrochloride solution thus obtained, so that a crystalline DM hydrochloride is formed. This crystallization step may be carried out by, after the addition of the aforesaid solvent for crystallization purposes, allowing the solution to stand at a temperature of about 5 to 35° C. and preferably at room temperature (18 to 27° C.), optionally with cooling (to about 5° C.) and optionally with gentle stirring. The crystalline DM hydrochloride so precipitated may be collected by a per se known technique such as filtration or centrifugation.

DM hydrochloride may be obtained as a commercial product, or may be prepared according to the process described in is Japanese Patent Laid-Open No. 21394/1'84 (corresponding to U.S. Pat. No. 4,592,999). As the starting material for use in the process of the present invention, the DM hydrochloride which has been obtained by any method may be used, provided that it suits the purpose of the present invention. However, it is generally favorable to use DM hydrochloride having a purity of not less than 90% and preferably not less than 95%.

The present invention is more specifically explained with reference to the following examples. However, it is not intended to limit the present invention to any of these examples.

EXAMPLE 1

Comparative Example 2 g of DM hydrochloride was dissolved in 20 mL of methanol. At room temperature, 200 mL of acetone was added to the solution, resulting in the formation of a precipitate. This precipitate was collected by filtration and dried (under reduced pressure at 60° C. for 16 hours) to obtain 1.2 g of a reddish-brown powder. The result of measurement of this powder according to the X-ray powder diffraction method is shown as a) in FIG. 1. The measuring conditions included a step angle of 0.02°, a counting time of 1.0 second, a tube voltage of 40.0 kV, and a tube current of 20.0 mA (the same shall apply hereinafter).

EXAMPLE 2

The Present Invention 2 g of DM hydrochloride was dissolved in 20 mL of methanol. At room temperature, 200 mL of 1-butanol was added to the solution, resulting in the formation of a precipitate. This precipitate was collected by filtration and dried (under reduced pressure at 60° C. for 16 hours) to obtain 1.4 g of a reddish-brown crystalline powder. The result of measurement of this powder according to the X-ray powder diffraction method is shown as b) in FIG. 1.

EXAMPLE 3

Comparative Example 2 g of DM hydrochloride was dissolved in 20 mL of methanol. At room temperature, 200 mL of ethanol was added to the solution, resulting in the formation of a precipitate. This precipitate was collected by filtration and dried (under reduced pressure at 60° C. for 16 hours) to obtain 0.9 g of a reddish-brown crystalline powder. The result of measurement of this powder according to the X-ray powder diffraction method is shown as c) in FIG. 1.

EXAMPLE 4

Comparative Example 2 g of DM hydrochloride was dissolved in 20 mL of methanol. At room temperature, 200 mL of diethyl ether was added to the solution, resulting in the formation of a precipitate. This precipitate was collected by filtration and dried (under reduced pressure at 60° C. for 16 hours) to obtain 1.5 g of a reddish-brown powder. The result of measurement of this powder according to the X-ray powder diffraction method is shown as d) in FIG. 1.

EXAMPLE 5

Comparative Example 2 g of DM hydrochloride was dissolved in 20 mL of methanol. At room temperature, 200 mL of 1-propanol was added to the solution, resulting in the formation of a precipitate. This precipitate was collected by filtration and dried (under reduced pressure at 60° C. for 16 hours) to obtain 0.9 g of a reddish-brown powder. The result of measurement of this powder according to the X-ray powder diffraction method is shown as e) in FIG. 1.

EXAMPLE 6

Comparative Example 2 g of DM hydrochloride was dissolved in 20 mL of methanol. At room temperature, 200 mL of 2-propanol was added to the solution, resulting in the formation of a precipitate. This precipitate was collected by filtration and dried (under reduced pressure at 60° C. for 16 hours) to obtain 1.3 g of a reddish-brown powder. The result of measurement of this powder according to the X-ray powder diffraction method is shown as f) in FIG. 1.

EXAMPLE 7

Comparative Example 2 g of DM hydrochloride was dissolved in 20 mL of methanol. At room temperature, 200 mL of n-hexane was added to the solution, resulting in the formation of a precipitate. This precipitate was collected by filtration and dried (under reduced pressure at 60° C. for 16 hours) to obtain 1.3 g of a reddish-brown crystalline powder. The result of measurement of this powder according to the X-ray powder diffraction method is shown as g) in FIG. 1.

EXAMPLE 8

Comparative Example 2 g of DM hydrochloride was dissolved in 20 mL of methanol. At room temperature, 200 mL of isopropyl ether was added to the solution, resulting in the formation of a precipitate. This precipitate was collected by filtration and dried (under reduced pressure at 60° C. for 16 hours) to obtain 1.6 g of a reddish-brown crystalline powder. The result of measurement of this powder according to the X-ray powder diffraction method is shown as h) in FIG. 1.

EXAMPLE 9

The Present Invention 0.5 g of DM hydrochloride was dissolved in 5 mL of methanol. At room temperature, 50 mL of a mixture (2:3) of 1-butanol and acetone was added to the solution, resulting in the formation of a precipitate. This precipitate was collected by filtration and dried (under reduced pressure at 60° C. for 16 hours) to obtain 0.28 g of a reddish-brown crystalline powder. The result of measurement of this powder according to the X-ray powder diffraction method showed the same pattern as that of b) in FIG. 1.

EXAMPLE 10

The Present Invention 0.5 g of DM hydrochloride was dissolved in 5 mL of methanol. At room temperature, 50 mL of a mixture (3:2) of 1-butanol and hexane was added to the solution, resulting in the formation of a precipitate. This precipitate was collected by filtration and dried (under reduced pressure at 60° C. for 16 hours) to obtain 0.38 g of a reddish-brown crystalline powder. The result of measurement of this powder according to the X-ray powder diffraction method showed the same pattern as that of b) in FIG. 1.

EXAMPLE 11

The Present Invention 0.5 g of DM hydrochloride was dissolved in 5 mL of methanol. At room temperature, 50 mL of a mixture (3:2) of 1-butanol and diisopropyl ether was added to the solution, resulting in the formation of a precipitate. This precipitate was collected by filtration and dried (under reduced pressure at 60° C. for 16 hours) to obtain 0.38 g of a reddish-brown crystalline powder. The result of measurement of this powder according to the X-ray powder diffraction method showed the same pattern as that of b) in FIG. 1.

EXAMPLE 12

Tests for Hygroscopicity

Samples of the powders (or crystalline powders) obtained in Examples 1–8 were stored at 30° C. and at relative humidities ranging from 32 to 91%. Their moisture contents were measured until a steady state was reached. The critical relative humidities calculated from the increases or decreases in moisture content are shown in Table 1 below.

TABLE 1

| Powder | Ex.1 | Ex.2 | Ex.3 | Ex.4 | Ex.5 | Ex.6 | Ex.7 | Ex.8 |
|---|---|---|---|---|---|---|---|---|
| Critical relative humidity (%) | 34 | 73 | 41 | 28 | 29 | 29 | 41 | 53 |

It can be seen from the above-described results that the crystalline DM hydrochloride obtained in Example 2 (the present invention) has very low hygroscopicity.

EXAMPLE 13

Tests for Chemical Stability

Each of the same samples as used in Example 12 was placed in a hermetically sealed container and stored at 60° C. for 1 month. Then, the sample was analyzed by HPLC to determine the DM content in the sample. The results thus obtained are shown in Table 2 below.

TABLE 2

| Powder | Ex.1 | Ex.2 | Ex.3 | Ex.4 | Ex.5 | Ex.6 | Ex.7 | Ex.8 |
|---|---|---|---|---|---|---|---|---|
| Amount of remaining DM (%) | 91.4 | 100 | 97.1 | 90.4 | 97.5 | 94.2 | 97.2 | 96.5 |

It can be seen from the above-described results that the crystalline powder of Example 2 has excellent chemical stability.

(Conditions for Analysis by HPLC)

Column: YMC A-312 (ODS) (manufactured by YMC Co., Ltd.).

Mobile phase: Acetonitrile-water (38:62) (adjusted to pH 2.2 with phosphoric acid).

Flow velocity: About 1.5 ml/min.

Detection: 254 nm.

EXAMPLE 14

Residual Solvent Content

Each of the same samples as used in Example 12 was analyzed by gas chromatography (GC) to determine its residual solvent content. The results thus obtained are shown in Table 2 below.

TABLE 3

| Powder | Crystalline form | | | | | | | |
|---|---|---|---|---|---|---|---|---|
| | Ex.1 | Ex.2 | Ex.3 | Ex.4 | Ex.5 | Ex.6 | Ex.7 | Ex.8 |
| Residual solvent content (%) | 0.14 | 0.40 | 0.03 | 0.50 | 0.19 | 0.18 | 0.05 | 0.95 |

It can be seen from the above-described results that the residual solvent content of the crystalline powder of Example 2 is within an acceptable limit.

(Operating Conditions for Analysis by GC)

Detector: Flame ionization detector.

Column: Shimadzu CBP 10-S25-050.

Column temperature: Operated at 40° C. for 5 minutes, and then raised to 80° C. in 5 minutes and held at that temperature.

Vaporization chamber temperature: A constant temperature around 200°.

Carrier gas: Helium.

Flow rate: A constant flow rate at which the retention time of an internal standard substance (dioxane) is about 6 minutes.

Exploitability in Industry

The present invention provides crystalline forms of DM hydrochloride showing a reduction in hygroscopicity and residual solvent content and an improvement in chemical stability, as well as a process which can produce them easily. Accordingly, the present invention may be utilized, for example, in the field of the manufacture of medicines and bulk materials for medicines.

What is claimed is:

1. A crystalline form of anthracycline antibiotic represented by the following formula (I) and having at least characteristic 2θ values in degrees of 6.18, 7.88, 9.82, 11.60, 13.30, 15.80, 20.88 and 23.12 as measured by an X-ray powder diffraction method:

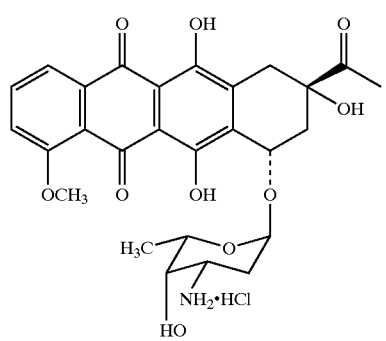

(I)

2. A process for producing a crystalline form of anthracycline antibiotic represented by the following formula (I) and having at least characteristic 2θ values in degrees of 6.18, 7.88, 9.82, 11.60, 13.30, 15.80, 20.88 and 23.12 as measured by an X-ray powder diffraction method,

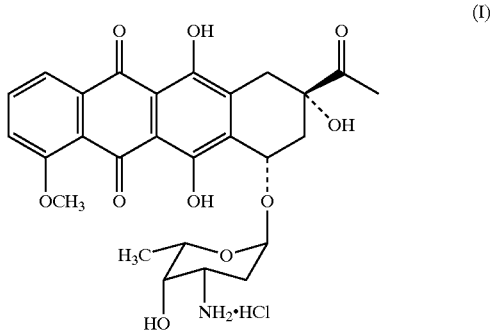

(I)

the process comprising the steps of:

preparing a solution comprising a first solvent comprising 1-butanol, a second solvent which is miscible with the first solvent and capable of dissolving the antibiotic of formula (I), and the antibiotic of formula (I) dissolved therein; and subjecting the solution to a crystallization treatment, to obtain said crystalline form of the antibiotic of formula (I).

3. The process as claimed in claim 2, wherein the first solvent is selected from the group consisting of 1-butanol, 1-butanol/acetone, 1-butanol/hexane and 1-butanol/diisopropyl ether.

4. The process as claimed in claim 2, wherein the first solvent is selected from the group consisting of butanol, 1-butanol/acetone, 1-butanol/hexane and 1-butanol/diisopropyl ether, and wherein the second solvent is selected from the group consisting of water, methanol, ethanol and a combination thereof.

5. The process as claimed in claim 2, which comprises the steps of dissolving 1 part by weight of the antibiotic of formula (I) in 5 to 20 parts by weight of methanol, adding 1-butanol or a solvent mixture comprising 1-butanol/acetone, 1-butanol/hexane or 1-butanol/diisopropyl ether in an amount of 1 to 20 parts by volume based on the volume of methanol, and crystallizing the antibiotic at a temperature in the range of 5 to 35° C.

6. The process as claimed in claim 5, wherein a solvent mixture is added, which comprises up to 60% by weight of acetone, hexane or diisopropyl ether.

* * * * *